United States Patent [19]

Bléjean et al.

[11] Patent Number: 5,536,695
[45] Date of Patent: Jul. 16, 1996

[54] DEHYDROGENATION CATALYSTS FOR $C_3C_{20}$ PARAFRINS, AND PREPARATION THEREOF

[75] Inventors: Franck Bléjean, Paris; Fabienne Le Pettier; Blaise Didillon, both of Rueil Malmaison, all of France

[73] Assignee: Institut Francais Du Petrole, Rueil Malmaison, France

[21] Appl. No.: 357,026

[22] Filed: Dec. 16, 1994

[30] Foreign Application Priority Data

Dec. 16, 1993 [FR] France .................. 93 15276

[51] Int. Cl.⁶ .................................................. B01J 23/40
[52] U.S. Cl. .................... 502/327; 502/328; 502/330; 502/524
[58] Field of Search ................... 502/328, 327, 502/330, 524

[56] References Cited

U.S. PATENT DOCUMENTS

| | | | |
|---|---|---|---|
| 4,486,547 | 12/1984 | Imai et al. | 502/328 |
| 4,608,360 | 8/1986 | Abrevaya et al. | 502/328 |
| 4,786,625 | 11/1988 | Imai et al. | 502/327 |
| 4,914,075 | 4/1990 | Bricker et al. | 502/327 |
| 5,219,816 | 6/1993 | Zhau et al. | 502/223 |
| 5,356,851 | 10/1994 | Sorrazin et al. | 502/328 |

FOREIGN PATENT DOCUMENTS

| | | |
|---|---|---|
| 0029321 | 5/1981 | European Pat. Off. . |
| 0166359 | 1/1986 | European Pat. Off. . |
| 0328507 | 8/1989 | European Pat. Off. . |
| 0360445 | 3/1990 | European Pat. Off. . |
| 0407115 | 1/1991 | European Pat. Off. . |
| 0448858 | 10/1991 | European Pat. Off. . |
| 1570521 | 2/1968 | France . |
| 2657126 | 6/1977 | Germany . |

*Primary Examiner*—Asok Pal
*Attorney, Agent, or Firm*—Millen, White, Zelano & Branigan

[57] ABSTRACT

The invention concerns a catalyst containing a support comprising at least one metal from group VIII of the periodic classification of elements such as platinum, palladium, ruthenium, rhodium, nickel, osmium or iridium, at least one additional metal selected from the group formed by groups IIB, IIIA, IVA, IVB, VA, VB, VIIB and VIII and at least one metal selected from the group formed by alkali and alkaline-earth metals, characterized in that said alkali or alkaline-earth metal is at least partially contained in the support in the form of an aluminate. The invention also concerns the preparation and use of said catalyst for dehydrogenation of $C_3$–$C_{20}$ paraffins.

14 Claims, No Drawings

DEHYDROGENATION CATALYSTS FOR $C_3C_{20}$ PARAFFINS, AND PREPARATION THEREOF

The present invention concerns a catalyst containing a support, its preparation and its use in converting $C_3$–$C_{20}$ paraffin hydrocarbons, i.e., hydrocarbons containing 3 to 20 carbon atoms per molecule, preferably $C_5$–$C_{20}$ paraffin hydrocarbons, to the corresponding olefins, the catalyst being characterised in that said support contains at least one alkali and/or alkaline-earth metal which is at least partially in the form of an aluminate.

Hydrocarbon dehydrogenation is an important industrial process because of the current demand for mono-olefins for the preparation of biodegradable detergents or pharmaceutical products, for example.

A large number of conventional catalysts containing an element from the platinum group, a second element from, for example, groups IIB, IIIA, IVA, IVB, VA, VB, VIIB and VIII, such as tin, germanium, lead, iridium, rhenium, indium, titanium, tungsten, or chromium, and an alkali or alkaline-earth metal such as potassium or lithium, have been developed for the dehydrogenation of $C_5^+$ paraffins, i.e., paraffins containing at least 5 carbon atoms per molecule, to produce the corresponding olefins (U.S. Pat. No. 4,827,072, for example).

During hydrocarbon transformation operations where catalysts are used, the activity of the catalyst progressively diminishes, mainly due to the accumulation of carbon deposits on the catalyst. The catalyst must then be regenerated. The usual regeneration techniques for platinum based catalysts generally comprise a coke elimination step involving heating the catalyst in an gas containing oxygen, then a redispersion step for the metallic phase by treating the catalyst with a gas containing chlorine and oxygen. These regeneration processes, however, deposit chlorine on the catalyst which leads to an increase in the acidity of the support. This phenomenon can lead to unwanted secondary reactions such as cracking, aromatisation and skeletal isomerisation, reducing the selectivity and stability of the catalyst. For the application envisaged, then, the catalyst must be regenerated using a process which does not increase the acidity of the support. Currently, coked catalysts are regenerated by heat treating the catalyst in a gas containing oxygen. However, this treatment usually leads to an aggregation of the metallic particles in the catalyst and thus leads to a loss in activity.

It is thus important to develop $C_3$–$C_{20}$, preferably $C_5$–$C_{20}$, paraffin hydrocarbon dehydrogenation catalysts which have improved stability and regeneration properties.

The invention thus concerns a supported catalyst, i.e., a catalyst containing a support, comprising at least one metal from group VIII such as platinum, palladium, ruthenium, rhodium, nickel, osmium and iridium, and at least one additional metal selected from the group formed by groups IIB, IIIA, IVA, IVB, VA, VB, VIIB and VIII, characterised in that said support contains at least one metal selected from the group formed by alkali and alkaline-earth metals, at least partially in the form of an aluminate. The invention also concerns the preparation of said catalyst and its use in the conversion of $C_3$–$C_{20}$, preferably $C_5$–$C_{20}$, paraffin hydrocarbons to the corresponding olefins.

During dehydrogenation of $C_3$–$C_{20}$, preferably $C_5$–$C_{20}$, paraffin hydrocarbons, the performance of the catalyst of the invention is improved compared to a conventional catalyst. The yield stability in particular is improved. In addition, the catalyst can be regenerated more effectively than a conventional catalyst, since this regeneration involves a reduced loss in catalytic performance. It can thus be regenerated more often before it is no longer considered usable. The support of the catalyst of the invention is characterised in that it comprises at least one metal selected from the group formed by alkali and alkaline-earth metals, at least partially in the form of an aluminate. The aluminate may, for example, be formed from alumina using the preparation process of the present description. The alumina generally has a specific surface area of between 50 and 600 m²/g, preferably between 70 and 400 m²/g. Apart from the characterising alkali and/or alkaline-earth metal aluminate, the support comprises any element known to the skilled person as a catalyst support, in particular alumina. The alkali or alkaline-earth metal is selected from the group formed by lithium, sodium, potassium, caesium, magnesium, strontium and calcium, preferably lithium and potassium, more preferably lithium. The quantity of metal in the aluminate form is between 20% and 100%, preferably between 50% and 100% of the total amount of metal, particularly when the metal is lithium.

The group VIII metal is selected from the following elements: platinum, palladium, ruthenium, rhodium, nickel, osmium and iridium, preferably platinum.

The additional metal is selected from the group formed by elements from groups IIB, IIIA, IVA, IVB, VA, VB, VIIB and VIII, preferably germanium, tin, indium, iron, iridium, rhenium, zinc, titanium, tungsten and chromium, preferably indium and tin.

The catalyst of the invention contains, by weight with respect to the support, between 0.2% and 13%, preferably between 0.5% and 4%, of alkali and/or alkaline-earth metal, between 0.1% and 2% of the group VIII metal and between 0 and 4%, more particularly between 0.01% and 4%, preferably between 0.1% and 3% of the additional metal. If the support comprises at least two noble metals, the content (in weight %) is the total content of noble metals. If the support contains at least two alkali metals, the content (in weight %) is the total alkali metal content. If the support contains at least two additional metals, the content (in weight %) is the total additional metal content.

The catalyst of the invention can, for example, be prepared by using any technique known to the skilled person to deposit an alkali and/or alkaline-earth metal on a support containing alumina in a first step, followed by a second step comprising treatment at a temperature of between 600° C. and 900° C., preferably between 650° C. and 800° C., said treatment leading to at least partial formation of the aluminate of said metal characterised by the corresponding diffraction lines. In the case where the metal used is lithium, for example, X ray diffraction analysis of the support shows the presence of lithium aluminates ($LiAl_5O_8$ and/or $LiAlO_2$). Any alkali and/or alkaline-earth metal aluminate is characterised by at least one diffraction line given in standard tables such as ASTM tables. The alkali and/or alkaline-earth metal compound deposited may, for example, be a carbonate, nitrate, acetate or hydroxide. The third step in preparing the catalyst of the invention consists in depositing, usually using conventional impregnation techniques, at least one additional metal and at least one metal from group VIII. The additional metal compound may, for example, be an inorganic compound such as a stannate, tartarate, oxalate or nitrate, or an organometallic compound such as tetrabutyltin or tributyltin hydride in the case of tin, or tetra-butylgermanium or germanium oxide in the case of germanium. The group VIII metal compound may, for example, be selected from the group formed by platinum dihydroxytetramine, platinum diaminonitrite, platinum dihydro-hexahydroxyplatinate or platinum acetylacetonate in the case of platinum. The additional metal and group VIII metal can be deposited in any order or using a common solution of said metals. When, for example, two separate solutions are used, the drying, calcining or reducing steps may take place between the two impregnation steps.

The final step in preparing the catalyst of the invention is usually a drying and/or calcining step, for example by heating the catalyst to a temperature between 250° C. and 600° C., in a gas containing molecular oxygen, for example air. Calcining can be carried out in situ, following loading of the catalyst into the dehydrogenation reactor, or it can be carried out ex situ. It may be followed by a reduction step under conditions known to the skilled person.

Any other preparation method known to the skilled person can also be employed, for example direct preparation of the support containing the alkali and/or alkaline-earth metal aluminate, followed by deposition of the other metals.

Dehydrogenation of $C_3$–$C_{20}$, preferably $C_5$–$C_{20}$, paraffin feedstocks is generally carried out at a pressure of between 0.2 and 20 bar, preferably between 0.5 and 5 bar, and at a temperature of between 400° C. and 800° C., preferably between 350° C. and 550° C. depending on the selected operating conditions. The hydrogen/hydrocarbon molar ratio is generally between 0 and 20, preferably between 0 and 10. The space velocity (in grams of hydrocarbon per gram of catalyst per hour) is generally between 20 and 150 $h^{-1}$. The operating conditions, which must take account of the nature of the treated feedstock, are adjusted by the skilled person to produce the best pressure-temperature-yield combination and activity.

After the reaction, the catalyst prepared in accordance with the invention can easily be regenerated using a technique involving heating the catalyst in a gas containing oxygen, to eliminate the carbon almost completely by combustion. This latter operation is carried out under conditions which are known to the skilled person.

The catalyst of the invention can be used in a pure chemical reaction or for hydrocarbon conversion: it is preferably used for dehydrogenation of $C_3$–$C_{20}$ hydrocarbons, more preferably for $C_5$–$C_{20}$ hydrocarbons.

The following non limiting examples illustrate the invention.

EXAMPLE 1 (comparative)

A dehydrogenation catalyst containing 0.31% of platinum, 0.80% of tin and 0.71% of lithium was prepared using techniques known to the skilled person.

90 $cm^3$ of an aqueous solution of lithium acetate containing 1.5 g of lithium was added to 150 g of an alumina support. This was left for 3 hours then dried for 1 hour at 120° C. and calcined for 2 hours at 350° C. at a VVH (volume space velocity) of 1500 $h^{-1}$. 90 $cm^3$ of an aqueous solution of tin acetate containing 1.2 g of tin was then added. The catalyst was dried for 1 hour at 120° C. and calcined for 2 hours at 530° C. Platinum was then introduced by adding 400 $cm^3$ of a solution of 0.9 g of platinum acetylacetonate in toluene. This was left for 24 hours then dried for 1 hour at 120° C. and calcined for 2 hours at 530° C. The catalyst obtained was termed catalyst A. X ray diffraction analysis showed the presence of diffraction lines corresponding to the starting alumina only (lines corresponding to d= $1.39 \cdot 10^{-10}$ m, d=$1.98 \cdot 10^{-10}$ m d=$2.39 \cdot 10^{-10}$ m and d=$2.28 \cdot 10^{-10}$ m).

EXAMPLE 2 (in accordance with the invention)

A dehydrogenation catalyst containing 0.31% of platinum, 0.80% of tin and 0.71% of lithium was prepared using techniques known to the skilled person.

90 $cm^3$ of an aqueous solution of lithium acetate containing 1.5 g of lithium was added to 150 g of an alumina support. This was left for 3 hours then dried for 1 hour at 120° C., and calcined for 2 hours at 750° C. at a VVH (volume of air per kilogram of catalyst per hour) of 2000 $h^{-1}$. 90 $cm^3$ of an aqueous solution of tin acetate containing 1.2 g of tin was then added. The catalyst was dried for 1 hour at 120° C. and calcined for 2 hours at 530° C. Platinum was then introduced by adding 400 $cm^3$ of a solution of 0.9 g of platinum acetylacetonate in toluene. This was left for 24 hours then dried for 1 hour at 120° C. and calcined for 2 hours at 530° C. The catalyst obtained was termed catalyst B. X ray diffraction analysis showed the presence of lithium aluminates (mainly $LiAl_5O_8$) characterised by lines at d= $2.38 \cdot 10^{-10}$ m, d=$1.40 \cdot 10^{-10}$ m, d=$1.98 \cdot 10^{-10}$ m and d=$2.80 \cdot 10^{-10}$ m in the presence of unmodified alumina.

EXAMPLE 3

Catalysts A and B, prepared in Examples 1 and 2 above, underwent a n-dodecane dehydrogenation test. 2 g of catalyst A or catalyst B were loaded into an isothermal reactor operating in descending flux mode. The catalyst was first reduced at 450° C. in a stream of hydrogen (2 l/h) at 450° C. The catalytic tests were carried out at a pressure of 2 bar absolute, with a molar ratio of hydrogen to hydrocarbons of 5 and a space velocity (in grams of hydrocarbon per gram of catalyst per hour) of 80 $h^{-1}$. The reaction temperature was held at 450° C. for 1 hour, then at 470° C. for 1 hour and finally at 450° C. for 1 hour ("return point").

The results obtained under these conditions are shown in Table 1.

TABLE 1

| Catalyst | Temperature (°C.) | $nC_{12}$ olefin conversion (wt %) | $nC_{12}$ olefin yeild (wt %) | aromatic yield (wt %) |
| --- | --- | --- | --- | --- |
| A | 450 | 10.4 | 9.6 | 0.3 |
|   | 470 | 12.1 | 10.3 | 0.8 |
|   | 450 | 6.0 | 5.6 | 0.1 |
| B | 450 | 10.2 | 9.2 | 0.2 |
|   | 470 | 14.2 | 12.2 | 0.7 |
|   | 450 | 8.2 | 7.5 | 0.2 |

Catalyst B, prepared in accordance with the invention, and in which the support partially comprises lithium aluminate, had higher olefin yields than those for catalyst A. In addition, the catalytic results corresponding to the "return point" at 450° C. show that catalyst B is more stable than catalyst A.

EXAMPLE 4

Following the catalytic tests carried out under the conditions of Example 3, catalysts A and B were regenerated to eliminate hydrocarbon deposits formed during the course of the reaction. This regeneration step was carried out by calcining the catalyst at 550° C. in a current of nitrogen containing oxygen. The oxygen content was adjusted so that the exothermicity of the combustion reaction did not cause more than a 5° C. increase in the temperature. Following regeneration, the catalyst was subjected to a new catalytic test using the conditions described in Example 3. The operations of the catalytic test and the regeneration step were together termed the "reaction-regeneration cycle". The results shown in Table 2 allow a comparison of the performance of catalysts A and B after 4 reaction-regeneration cycles.

TABLE 2

| Catalyst after 4 reaction-regeneration cycles | Temperature (°C.) | $nC_{12}$ olefin conversion (wt %) | $nC_{12}$ olefin yield (wt %) | aromatic yield (wt %) |
| --- | --- | --- | --- | --- |
| A | 450 | 7.4 | 6.8 | 0.1 |
|   | 470 | 10.7 | 9.2 | 0.4 |
|   | 450 | 6.8 | 6.2 | 0.1 |
| B | 450 | 10.7 | 9.8 | 0.2 |
|   | 470 | 13.7 | 12.3 | 0.2 |
|   | 450 | 8.3 | 7.8 | 0.04 |

After 4 reaction-regeneration cycles, catalyst B of the invention still performed better, regarding dehydrogenation of n-dodecane, than catalyst A.

We claim:

1. A catalyst comprising a support and a catalytic quantity of at least one metal selected from group VIII of the periodic classification of the elements, and at least one additional metal selected from the group consisting of metals of groups IIB, IIIA, IVA, IVB, VA, VB, VIIB and VIII, characterized in that said support comprises at least one metal aluminate selected from the group consisting of lithium aluminate and potassium aluminate, said aluminate having been formed by a process comprising calcining at above 600° C. prior to the introduction of the catalytic metals from groups IIB, IIIA, IIIB, IVA, IVB, VA, VB, VIIB and VIII.

2. A catalyst according to claim 1, in which the additional metal is selected from the group formed by indium and tin.

3. A catalyst according to claim 1 in which of said lithium or potassium metal 20% to 100% thereof is in aluminate form.

4. A catalyst according to claim 1 in which the metal selected is lithium.

5. A catalyst according to claim 1 comprising by weight between 0.1% and 2% of group VIII metal and between 0.1% and 13% of lithium or potassium.

6. Preparation of a catalyst in accordance with claim 1, comprising a first step of depositing at least one metal selected from the group formed by lithium and potassium metals on said support comprising alumina, a second step of calcining at a temperature of between 600° C. and 900° C., and a third step of depositing at least one noble metal and at least one additional metal.

7. Use of a catalyst according to claim 1 to convert paraffin hydrocarbons containing between 3 and 20 carbon atoms per molecule into the corresponding olefins.

8. Use of a catalyst according to claim 1 to convert paraffin hydrocarbons containing between 5 and 20 carbon atoms per molecule into the corresponding olefins.

9. A catalyst according to claim 1 in which the additional metal is selected from the group formed by germanium, tin, indium, iron, iridium, rhenium, zinc, titanium, tungsten and chromium.

10. A catalyst as in claim 1, wherein the potassium or lithium aluminate is formed by depositing potassium or lithium on alumina followed by treatment at a temperature between 650° C.–800° C.

11. A catalyst comprising a catalytic quantity of at least one metal selected from group VIII of the periodic classification of the elements and at least one additional metal selected from the group consisting of metals of groups IIB, IIIA, IVA, IVB, VA, VB, VIIB and VIII and a support wherein said support comprises potassium or lithium aluminate formed by depositing potassium or lithium on alumina followed by treatment at a temperature between 600° C.–900° C.

12. A catalyst comprising a catalytic quantity of at least one metal selected from the group VIII of the periodic classification of the elements and at least one additional metal selected from the group consisting of metals of groups IIB, IIIA, IVA, IVB, VA, VB, VIIA and VIII; and a support comprising alumina wherein said support further comprises lithium aluminum oxide.

13. A catalyst according to claim 11 wherein x-ray diffraction analysis of the support shows lines corresponding to the aluminates of lithium or potassium.

14. A catalyst according to claim 12 comprising oxide wherein x-ray diffraction analysis of the support shows lines corresponding to $d=2.38\times10^{-10}$ m, $d=1.40\times10^{-10}$ m, $d=1.98\times10^{-10}$ m and $d=2.80\times10^{-10}$ m for lithium aluminum oxide.

* * * * *